(12) United States Patent
Mirkin et al.

(10) Patent No.: US 7,807,372 B2
(45) Date of Patent: Oct. 5, 2010

(54) SCREENING SEQUENCE SELECTIVITY OF OLIGONUCLEOTIDE-BINDING MOLECULES USING NANOPARTICLE BASED COLORIMETRIC ASSAY

(75) Inventors: Chad A. Mirkin, Wilmette, IL (US); Sarah J. Hurst, Evanston, IL (US); Min Su Han, Kyung-Buk (KR); Abigail K. R. Lytton-Jean, Cambridge, MA (US)

(73) Assignee: Northwestern University, Evanston, IL (US)

( * ) Notice: Subject to any disclaimer, the term of this patent is extended or adjusted under 35 U.S.C. 154(b) by 304 days.

(21) Appl. No.: 12/133,243

(22) Filed: Jun. 4, 2008

(65) Prior Publication Data

US 2008/0311669 A1    Dec. 18, 2008

Related U.S. Application Data

(60) Provisional application No. 60/941,731, filed on Jun. 4, 2007.

(51) Int. Cl.
   C12Q 1/68    (2006.01)
   C07H 21/04    (2006.01)

(52) U.S. Cl. .......................... 435/6; 435/7.1; 536/23.1; 977/704; 977/924

(58) Field of Classification Search ........................ None
   See application file for complete search history.

(56) References Cited

U.S. PATENT DOCUMENTS

| | | |
|---|---|---|
| 3,687,808 A | 8/1972 | Merigan et al. |
| 4,489,055 A | 12/1984 | Couvreur et al. |
| 4,845,205 A | 7/1989 | Huynh Dinh et al. |
| 4,981,957 A | 1/1991 | Lebleu et al. |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,214,134 A | 5/1993 | Weis et al. |
| 5,216,141 A | 6/1993 | Benner |
| 5,235,033 A | 8/1993 | Summerton et al. |
| 5,264,562 A | 11/1993 | Matteucci |
| 5,264,564 A | 11/1993 | Matteucci |
| 5,319,080 A | 6/1994 | Leumann et al. |
| 5,359,044 A | 10/1994 | Cook et al. |
| 5,367,066 A | 11/1994 | Urdea et al. |

(Continued)

FOREIGN PATENT DOCUMENTS

WO    WO-97/12896    4/1997

(Continued)

OTHER PUBLICATIONS

Ahmadi et al., "Shape-controlled synthesis of colloidal platinum nanoparticles," *Science*, 272:1924-6 (1996).

Allara et al., "Spontaneously organized molecular assemblies. 1. Formation, dynamics and physical properties of n-Alkanoic acids adsorbed from solution on an oxidized aluminum surface," *Langmuir*, 1: 45 (1985).

(Continued)

*Primary Examiner*—B J Forman
(74) *Attorney, Agent, or Firm*—Marshall, Gerstein & Borun LLP

(57) ABSTRACT

Disclosed herein are methods of screening sequence selectivity of oligonucleotide-binding molecules using a gold nanoparticle based colorimetric assay.

15 Claims, 7 Drawing Sheets

U.S. PATENT DOCUMENTS

| | | | |
|---|---|---|---|
| 5,393,878 A | 2/1995 | Leumann et al. |
| 5,405,938 A | 4/1995 | Summerton et al. |
| 5,432,272 A | 7/1995 | Benner et al. |
| 5,434,257 A | 7/1995 | Matteucci et al. |
| 5,446,137 A | 8/1995 | Maag et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,134 A | 5/1996 | Acevedo et al. |
| 5,525,711 A | 6/1996 | Hawkins et al. |
| 5,539,082 A | 7/1996 | Nielsen et al. |
| 5,541,307 A | 7/1996 | Cook et al. |
| 5,552,540 A | 9/1996 | Haralambidis |
| 5,561,225 A | 10/1996 | Maddry et al. |
| 5,567,811 A | 10/1996 | Misiura et al. |
| 5,576,427 A | 11/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,361,944 B1 | 3/2002 | Mirkin et al. |
| 6,506,564 B1 | 1/2003 | Mirkin et al. |
| 6,750,016 B2 | 6/2004 | Mirkin et al. |
| 6,767,702 B2 | 7/2004 | Mirkin et al. |
| 7,238,472 B2 | 7/2007 | Mirkin et al. |
| 2002/0009733 A1* | 1/2002 | Lane et al. ............... 435/6 |
| 2003/0147966 A1 | 8/2003 | Franzen et al. |
| 2004/0219565 A1 | 11/2004 | Kauppinen et al. |
| 2005/0214782 A1 | 9/2005 | Chen et al. |

FOREIGN PATENT DOCUMENTS

| | | |
|---|---|---|
| WO | WO-98/04740 | 2/1998 |
| WO | WO-98/39352 | 9/1998 |
| WO | WO-99/14226 | 3/1999 |
| WO | WO-01/00876 | 1/2001 |
| WO | WO-01/51665 | 7/2001 |
| WO | WO-01/73123 | 10/2001 |
| WO | WO-02/096262 | 12/2002 |
| WO | WO-2007/047455 | 4/2007 |

OTHER PUBLICATIONS

Allara et al., "The study of the gas-solid interaction of acetic acid with a cuprous oxide surface using reflection-absorption spectroscopy," *J. Colloid Interface Sci.*, 49: 410-421 (1974).

Altschul et al., "Basic local alignment search tool," *J. Mol. Biol.*, 215: 403-410 (1990).

Baguley et al., "The interaction of ethidium with synthetic double-stranded polynucleotides at low ionic strength," *Nucleic Acids Res.*, 5: 161-171 (1978).

Bailly et al.,"Drug-DNA sequence-dependent interactions analysed by electric linear dichroism," *J. Molecul. Recogn.*, 5:155-171 (1992).

Boger et al., "A simple, high-resolution method for establishing DNA binding affinity and sequence selectivity," *J. Am. Chem. Soc.*, 123:5878-5891 (2001).

Boger et al., "Total synthesis of distamycin A and 2640 analogues: A solution-phase combinatorial approach to the discovery of new, bioactive DNA binding agents and development of a rapid, high-throughput screen for determining relative DNA binding affinity or DNA binding sequence selectivity," *J. Am. Chem. Soc.*, 122:6382-6394 (2000).

Brus, "Quantum crystallites and nonlinear optics," *Appl. Phys. A.*, 53: 465-474 (1991).

Burwell, "Modified silica gels as adsorbents and catalysts," *Chemical Technology*, 4, 370-377 (1974).

Charreyre et al., "Fluorescence energy transfer study of the conformation of oligonucleotides covalently bound to polystyrene latex particles," *Langmuir*, 13:3103-3110 (1997).

Chrisey et al., "Covalent attachment of synthetic DNA to self-assembled monolayer films," *Nucleic Acids Res.*, 24:3031-3039 (1996).

Coll et al., "A bifurcated hydrogen-bonded conformation in the d(A.T) base pairs of the DNA dodecamer d(CGCAAATTTGCG) and its complex with distamycin," *Proc. Natl. Acad. Sci. USA*, 84:8385-8389 (1987).

Curtis et al., "A morphology-selective copper organosol," *Angew. Chem. Int. Ed. Engl.*, 27:1530-1533 (1988).

De Mesmaeker et al., "Backbone modifications in oligonucleotides and peptide nucleic acid systems," *Curr. Opin. Struct. Biol.*, 5:343-355 (1995).

Eckstein (ed.), *Oligonucleotides and Analogues*, 1st Ed., New York, NY: Oxford University Press (1991).

Elaissari et al., "Effect of charge nature on the adsorption of single-stranded DNA fragments onto latex particles", *J. Colloid Interface Sci.*, 202:251-260(1998).

Elghanian et al., "Selective colorimetric detection of polynucleotides based on the distance-dependent optical properties of gold nanoparticles," *Science*, 277:1078-1081 (1997).

Eltekova et al., "Adsorption of aromatic compounds from solutions on titanium dioxide and silica",*Langmuir*, 3:951-957 (1987).

Englisch et al., "Chemically modified oligonucleotides as probes and inhibitors", *Angewandte Chemie, International Edition*, 30:613-629 (1991).

Enustun et al., "Coagulation of colloidal gold", *J Am Chem Soc*, 85:3317-3328 (1963).

Fahy et al., "Design and synthesis of polyacrylamide-based oligonucleotide supports or use in nucleic acid diagnostics," *Nucleic Acids Res.*, 21:1819-1826 (1993).

Fattal et al., "Biodegradable polyalkylcyanoacrylate nanoparticles for the delivery of oligonucleotides," *J. Control Release.*, 53:137-143 (1998).

Freier et al., "The ups and downs of nucleic acid duplex stability: structure-stability studies on chemically-modified DNA:RNA duplexes," *Nucleic Acids Res*, 25:4429-4443 (1997).

Grabar et al., "Preparation and characterization of Au colloid monolayers", *Anal Chem*, 67 : 735-743 (1995).

Han et al., "A gold nanoparticle based approach for screening triplex DNA binders," *J. Am. Chem. Soc.*, 128:4954-4955 (2006).

Han et al. "Colorimetric screening of DNA-binding molecules with gold nanoparticle probes", *Angew. Chem. International Edition*, 45:1807-1810 (2006).

Hayashi, "Ultrafine particles", *Vac. Sci. Technol.*, A5(4):1375-84 (1987).

Hayashi, "Ultrafine particles", *Physics Today*, pp. 44-60 (Dec. 1987).

Hayat (ed.), *Colloidal Gold: Principles, Methods, and Applications* (Academic Press, San Diego, 1991).

Henglein et al., "Adsorption spectrum and some chemical reactions of colloidal platinum in aqueous solution", *J Phys Chem*, 99: 14129-36 (1995).

Henglein, "Small-particle research: physiochemical properties of extremely small colloidal metal and small semiconductor particles", *Chem. Rev.*, 89:1861-1873 (1989).

Henglein, "Mechanism of reactions on colloidal microelectrodes and size quantization effects", *Top. Curr. Chem.*, 143:113-180 (1988).

Hickman et al., "Combining spontaneous molecular assembly with microfabrication to pattern surfaces: selective binding of isonitriles to platinum microwires and characterization by electrochemistry and surface spectroscopy", *J. Am. Chem. Soc.*, 111: 7271-7272 (1989).

Hubbard, "Electrochemistry of well-defined surfaces", *Acc. Chem. Res.*, 13:177-184 (1980).

Hurst et al., "Maximizing DNA loading on a range of gold nanoparticle sizes," *Anal Chem*, 78:8313-8318 (2006).

Iler, *The Chemistry Of Silica*, Chapter 6, New York: Wiley (1979).

Kolarova et al., "Preparation of magnetic oligo (dT) particles," *Biotechniques*, 20:196-198 (1996).

Kukowska-Latallo et al., "Efficient transfer of genetic material into mammalian cells using Starburst polyamidoamine dendrimers," *Proc. Natl. Acad. Sci. USA* , 93:4897-4902 (1996).

Lee et al., "Adsorption of ordered zirconium phosphonate multilayer films on silicon and gold surfaces", *J. Phys. Chem.*, 92 : 2597-601 (1988).

Liu et al., "New poly(d-glucaramidoamine)s induce DNA nanoparticle formation and efficient gene delivery into mammalian cells," *J. Am. Chem. Soc.* 126:7422-7423 (2004).

Lytton-Jean et al., "Microarray detection of duplex and triplex DNA binders with DNA-modified gold nanoparticles," *Anal. Chem*, 79:6037-6041 (2007).

Maoz et al., "Penetration-controlled reactions in organized monolayer assemblies. 1. Aqueous permanganate interaction with monolayer and multilayer films of long-chain surfactants", *Langmuir*, 3:1034-1044 (1987).

Maoz et al., "Penetration-controlled reactions in organized monolayer assemblies. 2. Aqueous permanganate interaction with self-assembling monolayers of long-chain surfactants," *Langmuir*, 3:1045-1051 (1987).

Marinakos et al., "Template synthesis of one-dimensional Au, Au-poly(pyrrole), and poly(pyrrole) nanoparticle arrays", *Chem Mater*, 10:1214-19 (1998).

Marinakos et al., "Gold nanoparticles as templates for the synthesis of hollow nanometer-sized conductive polymer capsules", *Ad. Mater*, 11:34-37 (1999).

Massart, "Preparation of aqueous magnetic liquids in alkaline and acidic media", *IEEE Transactions on Magnetics*, 17:1247-8 (1981).

Matteucci et al., "Synthesis of deoxyoligonucleotides on a polymer support", *J Am Chem Soc*, 103, 3185-3191 (1981) .

Mirkin et al., "A DNA-based method for rationally assembling nanoparticles into macroscopic materials," *Nature*, 382:607-609 (1996).

Matijevic (ed.), "Fine particles part II: Formation mechanisms and applications", *MRS Bulletin*, pp. 16-47 (Jan. 1990).

Mucic et al., "Synthesis and characterization of DNA with ferrocenyl groups attached to their 5-termini: electrochemical characterization of a redox-active nucleotide monolayer", *Chem Commun*, 555-557 (1996).

Nielsen et al., "Sequence-selective recognition of DNA by strand displacement with a thymine-substituted polyamide," *Science*, 254:1497-1500 (1991) .

Nuzzo et al., "Spontaneously organized molecular assemblies. 3. Preparation and properties of solution adsorbed monolayers of organic disulfides on gold surfaces," *J Am Chem Soc*, 109:2358-2368 (1987).

Nygren et al., "The interactions between the fluorescent dye thiazole orange and DNA," *Biopolymers*, 46:39-51 (1998).

Olshavsky et al., "Organometallic synthesis of gallium-arsenide crystallites, exhibiting quantum confinement", *J Am Chem Soc*, 12: 94389 (1990).

Pelton et al., "Structural characterization of a 2:1 distamycin A.d(CGCAAATTGGC) complex by two-dimensional NMR," *Proc. Natl. Acad. Sci. USA*, 86:5723-5727 (1989).

Ren et al., "Sequence and structural selectivity of nucleic acid binding ligands," *Biochemistry*, 38:16067-16075 (2000).

Rentzeperis et al., "Interaction of minor groove ligands to an AAATT/AATTT site: correlation of thermodynamic characterization and solution structure," *Biochemistry*, 34:2937-2945 (1995).

Sambrook et al., *Molecular Cloning: A Laboratory Manual* (2nd ed. 1989).

Sanghvi, "Heterocyclic base modifications in nucleic acids and their applications in antisense oligonucleotides", Chapter 15 in Crooke et al. (eds.), *Antisense Research and Applications*, CRC Press (1993).

Soriaga et al., "Determination of the orientation of aromatic molecules adsorbed on platinum electrodes. The effect of solute concentration", *J Am Chem Soc*, 104:3937-45 (1982).

Kroschwitz (ed.), *The Concise Encyclopedia of Polymer Science and Engineering*, pp. 858-859, New York: John Wiley & Sons (1990).

Timmons et al., "Investigation of fatty acid monolayers on metals by contact potential measurements", *J Phys Chem*, 69:984-990 (1965).

Tondelli, et al., "Highly efficient cellular uptake of c-myb antisense oligonucleotides through specifically designed polymeric nanospheres," *Nucleic Acids Res..*, 26:5425-5431 (1998).

Trauger et al., "Recognition of DNA by designed ligands at subnanomolar concentrations," *Nature*, 382:559-561 (1996).

Trauger et al. "Extension of sequence-specific recognition in the minor groove of DNA by pyrrole-imidazole polyamides to 9-13 base pairs", *J Am Chem Soc*. 118:6160-6166 (1996).

Tse et al., "A fluorescent intercalator displacement assay for establishing DNA binding selectivity and affinity," *Acc. Chem. Res.*, 37:61-69 (2004).

Turner et al., "The genome as a drug target: sequence specific minor groove binding ligands," *Curr Drug Targets*, 1:1-14 (2000).

Ushida et al., "GaAs nanocrystals prepared in quinoline", *J Phys Chem*, 95:5382-4 (1992).

Wan et al., "Non-covalent complexes between DNA-binding drugs and double-stranded oligodeoxynucleotides: A study by ESI ion-trap mass spectrometry", *J Am Chem Soc*, 122:300-307 (2000).

Wang et al., "Nanometer-sized semiconductor clusters : materials synthesis, quantum size effects, and photophysical properties", *J. Phys. Chem.*, 95: 525-532 (1991).

Wasserman et al., "Structure and reactivity of alkylsiloxane monolayers formed by reaction of alkyltrichlorosilanes on silicon substrates", *Langmuir*, 5:1074-1087 (1989).

Weller, "Colloidal semi-conductor Q-particles: Chemistry, in the transition region between solid state and molecules", *Angew. Chem. International Edition*, 32: 41-53 (1993).

Wemmer et al., "Targeting the minor groove of DNA," *Curr. Opin. Struct. Biol.*, 7:355-361 (1997).

White et al., "On the pairing rules for recognition in the minor groove of DNA by pyrrole-imidazole polyamides," *Chem. Biol.*, 4:569-578 (1997).

White et al., "Recogniton of the four Watson-Crick base pairs in the DNA minor groove by synthetic ligands," *Nature*, 391:468-471 (1998).

Whitesides, *Proceedings of the Robert A. Welch Foundation 39th Conference on Chemical Research Nanophase Chemistry*, Houston, Tex., pp. 109-121 (1995).

Wolf et al., "Rapid hybridization kinetics of DNA attached to submicron latex particles.," *Nucleic Acids Res*, 15:2911-2926 (1987).

Woynarowski, "Targeting critical regions in genomic DNA with AT-specific anticancer drugs," *Biochim. Biophys. Acta*, 1587:300-308 (2002).

Yang et al., "Structural studies of atom-specific anticancer drugs acting on DNA," *Pharmacol Therapy*, 83:181-215 (1999).

\* cited by examiner

SCREENING SEQUENCE SELECTIVITY OF OLIGONUCLEOTIDE-BINDING MOLECULES USING NANOPARTICLE BASED COLORIMETRIC ASSAY

CROSS-REFERENCE TO RELATED APPLICATIONS

This application claims the benefit of U.S. Provisional Application No. 60/941,731, filed Jun. 4, 2007, which is incorporated by reference in it entirety herein.

STATEMENT OF GOVERNMENT INTEREST

This invention was made with U.S. government support under National Science Foundation/Nanoscale Science and Engineering Center Grant No. EEC-0647560; Air Force Office of Scientific Research Grant No. F49620-01-1-0404; and National Cancer Institute/Centers of Cancer Nanotechnology Excellence Grant No. 1U54CA119341-01. The government has certain rights in this invention.

BACKGROUND

Researchers are striving to generate large libraries of DNA-binding molecules through rational design and combinatorial methods (see, e.g., Trauger, et al., *Nature*, 382, 559-561 (1996); Wemmer, et al., *Curr. Opin. Struct. Biol.*, 7, 355-361 (1997); White, S., et al. *Chem. Biol.*, 4, 569-578 (1997); White, et al. *Nature*, 391, 468-471 (1998); Boger, et al. *J. Am. Chem. Soc.*, 122, 6382-6394 (2000)). Classes of such molecules, which include, for example, doxorubicin, daunorubicin and amsacrine, can be used to regulate gene expression and are being developed as anti-cancer drugs (Yang, et al. *Pharma. Therap.*, 83, 181-215 (1999)). The development of high-throughput assays that can be used to quickly and efficiently evaluate these potential drug candidates is critical to progress in this area. Gold nanoparticle (Au NP)-based methods recently have been developed to screen for DNA duplex- and triplex-binding molecules both in solution and on the surface of a chip (Han, et al. *Angew. Chem. Int. Ed.*, 45, 1807-1810 (2006); Han, et al. *J. Am. Chem. Soc.*, 128, 4954-4955 (2006); Lytton-Jean, et al. *Anal. Chem*, 79, 6037-6041. (2007); and International Patent Publication No. WO 2007/047455).

Once a potential drug candidate is synthesized and its DNA binding capabilities confirmed, it is then vital to determine the selectivity of its binding for particular sequences of DNA. This information is crucial in targeting specific areas of the genome in certain therapeutic schemes (Woynarowski, *Biochim. Biophys. Acta*, 1587, 300-308 (2002) and Turner, et al. *Curr. Drug Targets*, 1, 1-14 (2000)). Unfortunately, most methods for evaluating the sequence selectivity of libraries of potential drug candidates are often inconvenient, especially for the purposes of large scale, high-throughput screening. Traditional biological techniques such as foot printing and affinity cleavage have thus far been the most commonly used methods (Trauger, et al. *J. Am. Chem. Soc.*, 118, 6160-6166 (1996)). More recently, mass spectroscopy, competition dialysis, NMR, calorimetry, circular dichroism, and x-ray diffraction also have been used (Wan, et al. *J. Am. Chem. Soc.*, 122, 300-307 (2000); Ren, et al. *Biochemistry*, 38, 16067-16075 (2000); Pelton, et al. *Proc. Natl. Acad. Sci. USA*, 86, 5723-5727 (1989); Rentzeperis, et al. *Biochemistry*, 34, 2937-2945 (1995); and Coll, et al. *Proc. Natl. Acad. Sci. USA*, 84, 8385-8389 (1987)). Only recently has a high-throughput, fluorescence-based method been developed to elucidate the sequence specificity of DNA-binding molecules (Boger, et al. *J. Am. Chem. Soc.*, 123, 5878-5891 (2001) and Tse, et al. *Acc. Chem. Res.*, 37, 61-69 (2004)).

Although useful, this fluorescent intercalator displacement (FID) assay has some weaknesses. First, the FID assay is an on-off system, where a relative decrease rather than an increase in signal is monitored. Second, the fluorescence signal of the reference intercalator (thiazole orange or ethidium bromide (EB)) often interferes with that of the DNA binding molecule of interest (Haugland, *Handbook of Fluorescent Probes and Research Products.* Molecular Probes, Eugene, Oreg. (2002)). Third, the fluorescence intensities of the intercalator/DNA complex are sometimes sensitive to the DNA sequence (Nygren, et al. *Biopolymers*, 46, 39-51 (1998)). Lastly, in the FID method, there is some error associated with the assumption that the reference intercalator has no selectivity for any particular DNA sequence. Although intercalators such as thiazole orange and ethidium bromide are considered non-specific binders, they in fact have slight preferences for certain sequences of DNA (Nygren, et al. *Biopolymers*, 46, 39-51 (1998) and Baguley, et al. *Nucleic Acids Res.*, 5, 161-171 (1978)). Thus, a need exists for an efficient method of screening libraries of molecules for DNA selectivity.

SUMMARY

Disclosed herein are methods of assessing the selectivity of an oligonucleotide-binding molecule using a functionalized nanoparticle based assay. More specifically, disclosed herein is a method of assessing selectivity of an oligonucleotide-binding molecule comprising:

a) heating a first mixture comprising (1) a first complex comprising a first functionalized nanoparticle and a second functionalized nanoparticle, (2) a first hairpin oligonucleotide, and (3) the oligonucleotide-binding molecule to determine a first melting temperature of the first complex in the first mixture, b) comparing the first melting temperature of the first complex in the first mixture to a second melting temperature of the first complex in a second mixture comprising (1) the first complex, (2) a second hairpin oligonucleotide; and (3) the oligonucleotide-binding molecule, wherein a first melting temperature different from the second melting temperature indicates a selectivity of the oligonucleotide-binding molecule compound for either the first hairpin oligonucleotide or for second hairpin oligonucleotide, and a first melting temperature essentially equal to the second melting temperature indicates essentially equal selectivity of the oligonucleotide-binding molecule for the second hairpin oligonucleotide and the first hairpin oligonucleotide. The functionalized nanoparticles used in the disclosed methods comprise a first oligonucleotide on at least a portion of the first nanoparticle surface, and the second functionalized nanoparticle comprises a second oligonucleotide on at least a portion of the second nanoparticle surface, wherein the first oligonucleotide is sufficiently complementary to the second oligonucleotide to hybridize, and the sequences of the first and second oligonucleotides and first and second hairpin oligonucleotide are of known sequences. The first and second oligonucleotides have different sequences from that of the first and second hairpin oligonucleotide sequence. In embodiments where the oligonucleotide-binding molecule is a destabilizing molecule, when the first melting temperature is higher than the second melting temperature, the molecule has a selectivity for the first hairpin oligonucleotide over that of the second hairpin oligonucleotide. In embodiments where the oligonucleotide-binding molecule is a stabilizing molecule, when the first melting temperature is higher than the second melting temperature, the molecule has a selectivity for the second hairpin oligonucleotide over that of the first hairpin oligonucleotide.

In various embodiments, the oligonucleotide used herein is DNA, RNA, a modified oligonucleotide, or both. In some embodiments, the nanoparticles used herein are metallic nanoparticles, and in specific embodiments, are gold nanoparticles. In certain aspects, the nanoparticles have a diameter of about 13 nm to about 250 nm.

DETAILED DESCRIPTION

Disclosed herein are methods of assessing sequence selectivity of an oligonucleotide-binding molecule using aggregates of oligonucleotide-functionalized gold nanoparticles (Au NPs), which is advantageous over prior methods, such as the FID method. The disclosed assay is an off-on system, where a color change in a solution of the Au NPs is monitored. The visible signal does not interfere with the signal from the oligonucleotide binding molecules that are being evaluated. This assay also does not need reference intercalators. Moreover, owing to the high extinction coefficient of Au NPs in the visible region, the readout of this nanoparticle-based assay can be analyzed with the naked eye without the need for complicated or expensive instrumentation.

The disclosed method differs from prior colorimetric screening using oligonucleotide- functionalized nanoparticles, as disclosed in International Patent Publication No. WO 07/047455, as the present method allows for assessment of sequence selectivity of an oligonucleotide-binding molecule. While the methods disclosed in WO 07/047455 allowed for identification of a potential oligonucleotide-binding molecule, the present method allows for determination of sequence selectivity of an oligonucleotide-binding molecule by comparing melting temperatures of a Au NP aggregate in the presence of the oligonucleotide-binding molecule and hairpin oligonucleotides of various sequences.

In general, when two Au NPs are modified with complementary oligonucleotide sequences and mixed, these nanoparticles aggregate to form complexes via hybridization of the complementary oligonucleotides (Mirkin, et al. *Nature*, 382, 607-609 (1996)). Throughout this disclosure, nanoparticle aggregates are alternatively referred to as complexes. Au NP aggregation is characterized by a red-to-blue color transition that is the result of the red shifting and dampening of the nanoparticle surface plasmon resonance (SPR) band. The aggregation is reversible and when these aggregates are heated, the oligonucleotides dehybridize (or melt) and the structures break apart. A melting transition for these nanoparticle-oligonucleotide aggregates is typically described in terms of a melting temperature ($T_m$) and the full width at half maximum (FWHM) of the first derivative of the transition. The melting transitions of these nanoparticle structures are dramatically sharper (FWHM of about 1-2° C.) than those for the corresponding free oligonucleotide duplexes that are not attached to nanoparticle surfaces, which have a FWHM of about 10-12° C. (Elghanian, et al. *Science*, 277, 1078-1081 (1997)). The examples herein use several specific sequences, but it will be appreciated by one of ordinary skill in the art that other sequences are readily amenable for use in the disclosed methods.

Figure 1A:
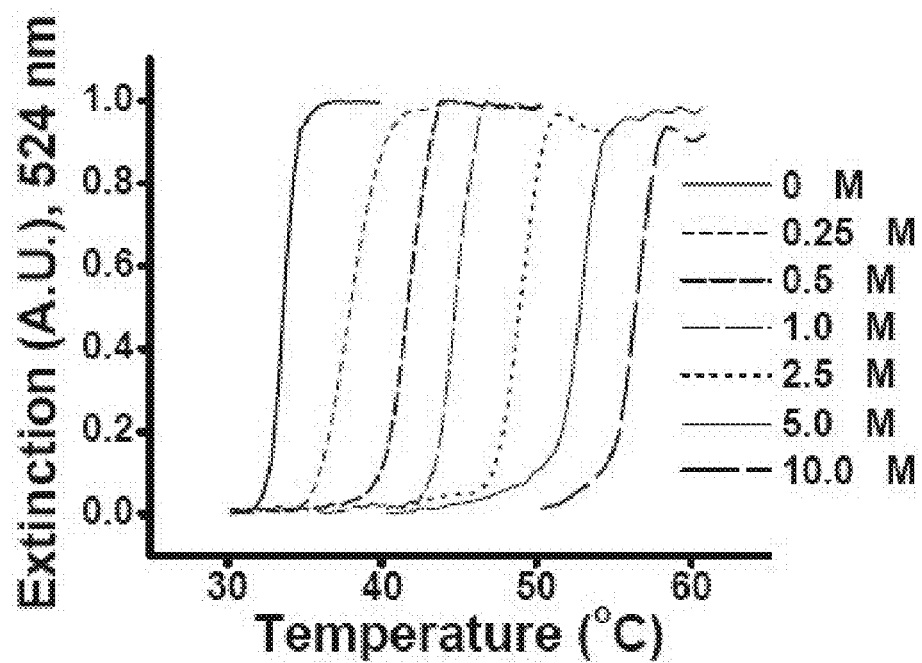
FIG. 1A shows normalized melting curves, monitored at the maximum in Au NP extinction ($\lambda$=524 nm), for aggregates of NP-1 and NP-2 for varying concentrations of DAPI between 0 and 10 μM.
Figure 1B:
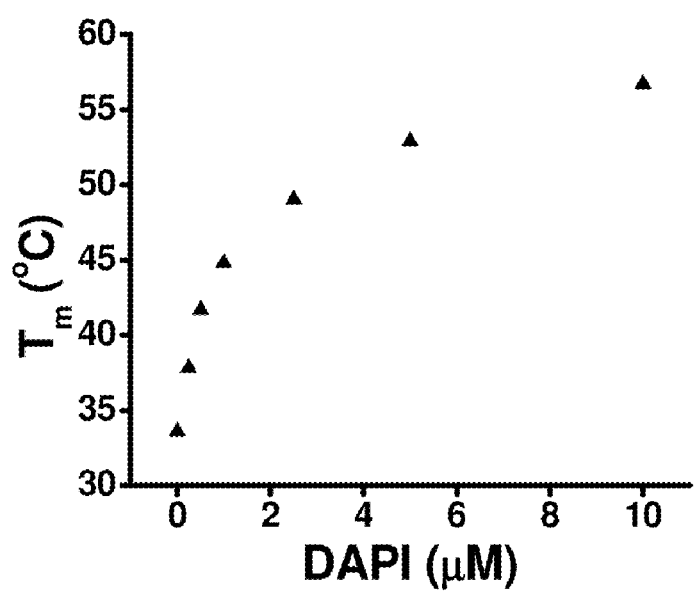
FIG. 1B shows the corresponding plot of melting temperature ($T_m$) vs. DAPI concentration.
Figure 2:
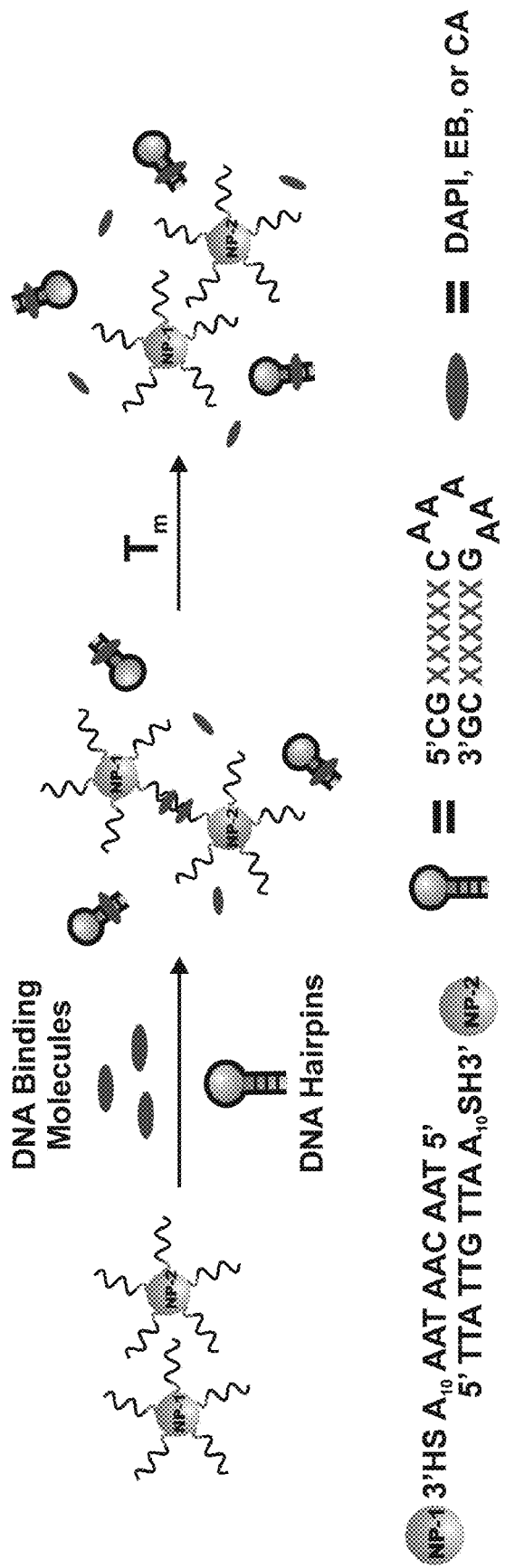
FIG. 2 shows a general scheme for screening the sequence selectivity of oligonucleotide binding molecules using functionalized Au NPs.

When an oligonucleotide-binding molecule is added to a solution containing aggregates of Au NPs having complexed oligonucleotides on their surfaces, the molecule can bind to the complexed oligonucleotides linking the nanoparticles and, depending upon whether the molecule is a stabilizing or destabilizing molecule, the molecule can stabilize or destabilize the aggregate structures. These interactions affect the $T_m$ of the Au NP aggregates (see FIGS. 1A and 1B). Stabilizing molecules binding to the Au NP aggregates increase the $T_m$, while destabilizing molecules decrease the $T_m$. The data show that the nanoparticle $T_m$ is sensitive to the concentration of the binding molecule in solution, and despite the presence of the binding molecule, the melting transitions of the nanoparticles remain sharp (about 1-2° C.), which allow for small differences in $T_m$ to be distinguished. These sensitivities allow for the determination of the molecule's selectivity for one sequence versus another—e.g., the sequence of the Au NP complexes or the sequence of the hairpin oligonucleotide within one mixture. Even small differences in preference for one sequence over another can be determined in the disclosed methods (see, e.g., FIG. 5).

The relationship between oligonucleotide-binding molecule concentration and nanoparticle $T_m$ to screen the selectivity of the molecule for a particular sequence. When the oligonucleotide-binding molecule is added to a solution having two complementary oligonucleotide-functionalized NPs and a hairpin oligonucleotide with a sequence different from those on the NPs, it can either bind to the oligonucleotides on the NPs or to the hairpin oligonucleotide, depending upon its relative affinity for each. Thus, by screening a series of different hairpin oligonucleotides and/or duplexed oligonucleotides on NPs, the selectivity of the oligonucleotide-binding molecule can be assessed.

Figure 4:
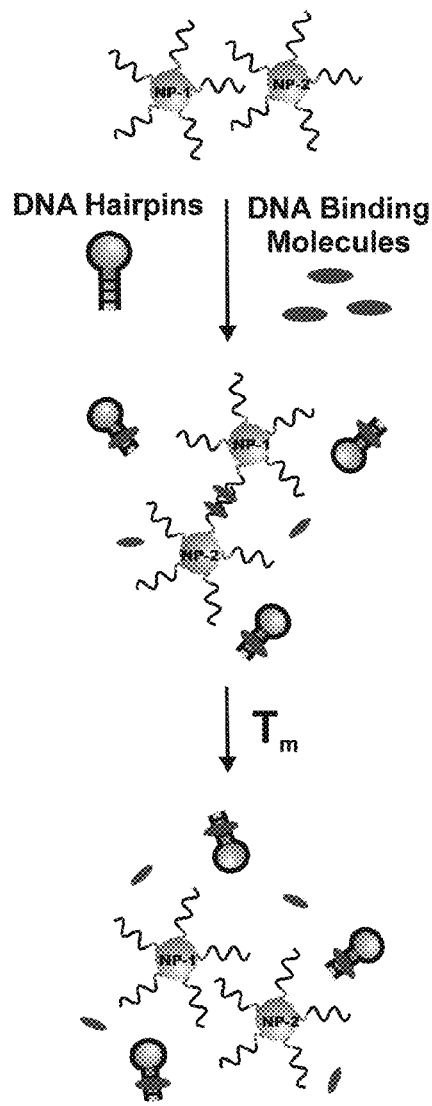
FIG. 4 shows a side-by-side comparison of the Au NP-based assay disclosed herein and the prior discloses FID assay.
Figure 4:
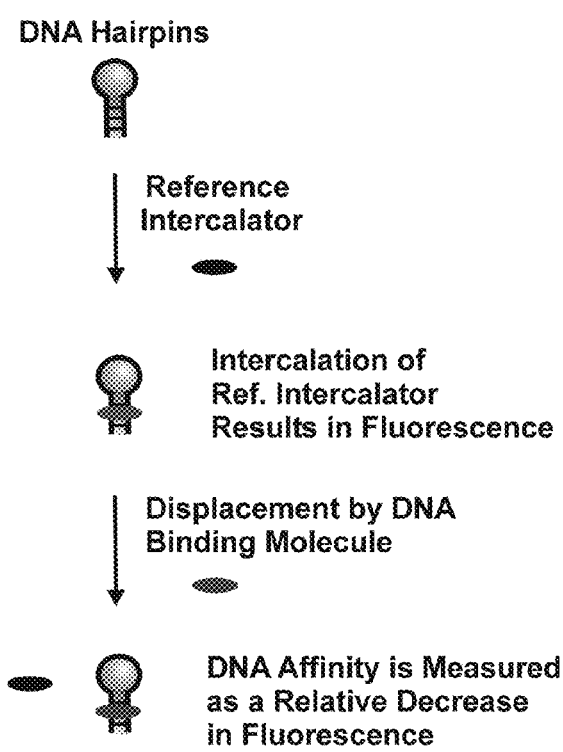

The disclosed method employs oligonucleotide-functionalized Au NPs to screen the sequence selectivity of oligonucleotide-binding molecules. This competition-based assay can differentiate between, e.g., AT-specific, non-specific, and GC-specific binding molecules, and has several benefits compared to previous systems. The disclosed method can be used to screen the selectivity of a variety of potential oligonucleotide-binding molecules in a high-throughput fashion. Further, the assay can be monitored using the naked eye, as the color change of the Au NPs from aggregates to deaggregated species is marked by a blue to red color change. Additionally, the method does not use reference intercalators, nor does the measured signal interfere with the signal from the oligonucleotide-binding molecules being evaluated. The readout of the assay can be analyzed with the naked eye without the need for complicated or expensive instrumentation, owing to the high extinction coefficient of Au NPs in the visible region of the spectrum. Also, as highlighted in FIG. 4, with this method direct comparison of the relative affinity of a possible intercalator for different sequences of DNA rather than the affinity of 2 intercalators (1 reference and 1 sample) for 1 sequence of DNA, can be performed. This method can be extended and modified to gauge the sequence selectivity of other types of oligonucleotide binding moieties, such as small molecules, proteins, metals, metal complexes, and oligonucleotide cross-linking molecules.

Oligonucleotide-Binding Molecules

As used herein, the term "oligonucleotide-binding molecule" or "intercalator," refers to a molecule capable of intercalating into an oligonucleotide duplex. "Intercalation" refers to the reversible or irreversible inclusion of, for example, a molecule between two other molecules. Of significance to the present methods, a large class of molecules, mostly polycyclic, aromatic, and planar, are known that intercalate into a double-strand polynucleotide between two adjacent base pairs. Examples of intercalators known in the art include ethidium, proflavin, daunomycin, doxorubicin, and thalidomide. Intercalators have the property of (i) interacting with an oligonucleotide complex without affecting stability of the hybridized complex, (ii) interacting with an oligonucleotide complex and increasing stability of the hybridized complex, or (iii) interacting with an oligonucleotide complex and decreasing stability of the hybridized complex. Still other intercalators have the ability to interact with bases in a single-strand oligonucleotide and prevent oligonucleotide complex formation. While not technically "intercalators" in the sense that it interacts with hybridized oligonucleotides, compounds of this type are readily identified in methods provided.

Complex Detection

Regardless of the type of oligonucleotide-binding molecule being identified, methods are provided wherein oligonucleotide complex formation (or separation) is detected by an observable change. In one aspect, complex formation (or separation) gives rise to a color change which is observed with the naked eye or spectroscopically. When using gold nanoparticles, a red-to-blue color change occurs with nanoparticle aggregation which often is detected with the naked eye. A blue-to-red color change occurs with nanoparticle de-aggregation, which is also detectable with the naked eye. In another aspect, oligonucleotide complex formation gives rise to aggregate formation which is observed by electron microscopy or by nephelometry. Aggregation of nanoparticles in general also gives rise to decreased plasmon resonance. In still another aspect, complex formation gives rise to precipitation of aggregated nanoparticles which is observed with the naked eye or microscopically.

The observation of a color change with the naked eye is, in one aspect, made against a background of a contrasting color. For instance, when gold nanoparticles are used, the observation of a color change is facilitated by spotting a sample of the hybridization solution on a solid white surface (such as, without limitation, silica or alumina TLC plates, filter paper, cellulose nitrate membranes, nylon membranes, or a C-18 silica TLC plate) and allowing the spot to dry. Initially, the spot retains the color of the hybridization solution, which ranges from pink/red, in the absence of hybridization, to purplish-red/purple, if there has been hybridization. On drying at room temperature or 80° C. (temperature is not critical), a blue spot develops if the nanoparticle-oligonucleotide conjugates had been linked by hybridization prior to spotting. In the absence of hybridization, the spot is pink. The blue and the pink spots are stable and do not change on subsequent cooling or heating or over time providing a convenient permanent record of the test. No other steps (such as a separation of hybridized and unhybridized nanoparticle-oligonucleotide conjugates) are necessary to observe the color change.

An alternate method for visualizing the results from practice of the methods is to spot a sample of nanoparticle probes on a glass fiber filter (e.g., Borosilicate Microfiber Filter, 0.7 micron pore size, grade FG75, for use with gold nanoparticles 13 nm in size), while drawing the liquid through the filter. Subsequent rinsing washes the excess, non-hybridized probes through the filter, leaving behind an observable spot comprising the aggregates generated by hybridization of the nanoparticle probes (retained because these aggregates are larger than the pores of the filter). This technique allows for greater sensitivity, since an excess of nanoparticle probes can be used.

Depending on experimental design, obtaining a detectable change depends on hybridization of different oligonucleotides, or disassociation of hybridized oligonucleotides, i.e., complex disassociation. Mismatches in oligonucleotide complementarity decrease the stability of the complex. It is well known in the art that a mismatch in base pairing has a much greater destabilizing effect on the binding of a short oligonucleotide probe than on the binding of a long oligonucleotide probe.

In other embodiments, the detectable change is created by labeling the oligonucleotides, the nanoparticles, or both with molecules (e.g., and without limitation, fluorescent molecules and dyes) that produce detectable changes upon hybridization of the oligonucleotides on the nanoparticles. In one aspect, oligonucleotides functionalized on nanoparticles have a fluorescent molecule attached to the terminus distal to the nanoparticle attachment terminus. Metal and semiconductor nanoparticles are known fluorescence quenchers, with the magnitude of the quenching effect depending on the distance between the nanoparticles and the fluorescent molecule. In the single-strand state, the oligonucleotides attached to the nanoparticles interact with the nanoparticles, so that significant quenching is observed. Upon polynucleotide complex formation, the fluorescent molecule will become spaced away from the nanoparticles, diminishing quenching of the fluorescence. Longer oligonucleotides give rise to larger changes in fluorescence, at least until the fluorescent groups are moved far enough away from the nanoparticle surface so that an increase in the change is no longer observed. Useful lengths of the oligonucleotides can be determined empirically. Thus, in various aspects, metallic and semiconductor nanoparticles having fluorescent-labeled oligonucleotides attached thereto are used in any of the assay formats described herein.

Methods of labeling oligonucleotides with fluorescent molecules and measuring fluorescence are well known in the art. Suitable fluorescent molecules are also well known in the art and include without limitation fluoresceins, rhodamines and Texas Red.

In yet another embodiment, two types of fluorescent-labeled oligonucleotides attached to two different particles can be used. Suitable particles include polymeric particles (such as, without limitation, polystyrene particles, polyvinyl particles, acrylate and methacrylate particles), glass particles, latex particles, Sepharose beads and others like particles well known in the art. Methods of attaching oligonucleotides to such particles are well known and routinely practiced in the art. See Chrisey et al., *Nucleic Acids Research*, 24, 3031-3039 (1996) (glass) and Charreyre et al., *Langmuir*, 13,3103-3110 (1997), Fahy et al., *Nucleic Acids Research*, 21,1819-1826 (1993), Elaissari et al., *J. Colloid Interface Sci.*, 202,251-260 (1998), Kolarova et al., *Biotechniques*, 20, 196-198 (1996) and Wolf et al., *Nucleic Acids Research*, 15, 2911-2926 (1987) (polymer/latex). In particular, a wide variety of functional groups are available on the particles or can be incorporated into such particles. Functional groups include carboxylic acids, aldehydes, amino groups, cyano groups, ethylene groups, hydroxyl groups, mercapto groups, and the like. Nanoparticles, including metallic and semiconductor nanoparticles, can also be used.

In aspects wherein two fluorophores are employed, the two fluorophores are designated "d" and "a" for donor and acceptor. A variety of fluorescent molecules useful in such combinations are well known in the art and are available from, e.g., Molecular Probes. An attractive combination is fluorescein as the donor and Texas Red as acceptor. The two types of nanoparticle-oligonucleotide conjugates with "d" and "a" attached are mixed, and fluorescence measured in a fluorimeter. The mixture is excited with light of the wavelength that excites d, and the mixture is monitored for fluorescence from a. Upon hybridization, "d" and "a" will be brought in proximity. In the case of non-metallic, non-semiconductor particles, hybridization is shown by a shift in fluorescence from that for "d" to that for "a" or by the appearance of fluorescence for "a" in addition to that for "d." In the absence of hybridization, the fluorophores will be too far apart for energy transfer to be significant, and only the fluorescence of "d" will be observed. In the case of metallic and semiconductor nanoparticles, lack of hybridization will be shown by a lack of fluorescence due to "d" or "a" because of quenching as discussed herein. Hybridization is shown by an increase in fluorescence due to "a." The person of ordinary skill in the art will readily appreciate that the discussion herein as it relates to formation of a double-strand complex, but that the use of two or three fluorophores can be utilized when a triplex polynucleotide complex is used in the method.

Other labels besides fluorescent molecules can be used, such as chemiluminescent molecules, which will give a detectable signal or a change in detectable signal upon hybridization.

Oligonucleotide complex formation (or separation) of NP aggregates, detected by any suitable means, in the presence of the (suspected) oligonucleotide-binding molecule is compared in the presence of various hairpin oligonucleotides having different sequences. Differences in the melting of complexes of the NP aggregates indicate a preference, or selectivity, of the oligonucleotide-binding molecule for the sequence of either the complex of the NP aggregates or of the hairpin oligonucleotide.

Nanoparticles

In general, nanoparticles (NPs) contemplated include any compound or substance with a high loading capacity for an oligonucleotide as described herein, including for example and without limitation, a metal, a semiconductor, and an insulator particle compositions, and a dendrimer (organic or inorganic).

Thus, nanoparticles are contemplated for use in the methods which comprise a variety of inorganic materials including, but not limited to, metals, semi-conductor materials or ceramics as described in U.S. Patent Publication No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In one embodiment, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example., ferromagnetite) colloidal materials. Other nanoparticles useful in the practice of the invention include, also without limitation, ZnS, ZnO, Ti, $TiO_2$, Sn, $SnO_2$, Si, $SiO_2$, Fe, $Fe^{+4}$, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.*, 53, 465 (1991); Bahncmann, in *Photochemical Conversion and Storage of Solar Energy* (eds. Pelizetti and Schiavello 1991), page 251; Wang and Herron, *J. Phys. Chem.*, 95, 525 (1991); Olshavsky, et al., *J. Am. Chem. Soc.*, 112, 9438 (1990); Ushida et al., *J. Phys. Chem.*, 95, 5382 (1992).

In practice, methods are provided using any suitable nanoparticle having oligonucleotides attached thereto that are in general suitable for use in detection assays known in the art to the extent and do not interfere with oligonucleotide complex formation, i.e., hybridization to form a double-strand or triple-strand complex. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles, aggregate particles, isotropic (such as spherical particles) and anisotropic particles (such as non-spherical rods, tetrahedral, prisms) and core-shell particles such as the ones described in U.S. Pat. No. 7,238,472 and International Patent Publication No. WO 2002/096262, the disclosures of which are incorporated by reference in their entirety.

Methods of making metal, semiconductor and magnetic nanoparticles are well-known in the art. See, for example, Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science,* 272, 1924 (1996); Henglein, A. et al., *J. Phys. Chem.,* 99, 14129 (1995); Curtis, A. C., et al., *Angew. Chem. Int. Ed. Engl.,* 27, 1530 (1988). Preparation of polyalkylcyanoacrylate nanoparticles prepared is described in Fattal, et al., *J. Controlled Release* (1998) 53: 137-143 and U.S. Pat. No. 4,489,055. Methods for making nanoparticles comprising poly(D-glucaramidoamine)s are described in Liu, et al., *J. Am. Chem. Soc.* (2004) 126:7422-7423. Preaparation of nanoparticles comprising polymerized methylmethacrylate (MMA) is described in Tondelli, et al., *Nucl. Acids Res.* (1998) 26:5425-5431, and preparation of dendrimer nanoparticles is described in, for example Kukowska-Latallo, et al., *Proc. Natl. Acad. Sci. USA* (1996) 93:4897-4902 (Starburst polyamidoamine dendrimers).

Suitable nanoparticles are also commercially available from, for example, Ted Pella, Inc. (gold), Amersham Corporation (gold) and Nanoprobes, Inc. (gold).

Also as described in US Patent Publication No. 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) *Vac. Sci. Technol.* July/August 1987, A5(4):1375-84; Hayashi, (1987) *Physics Today*, December 1987, pp. 44-60; MRS Bulletin, January 1990, pp. 16-47.

As further described in US Patent Publication No. 20030147966, nanoparticles contemplated are produced using $HAuCl_4$ and a citrate-reducing agent, using methods known in the art. See, e.g., Marinakos et al., (1999) *Adv. Mater.* 11: 34-37; Marinakos et al., (1998) *Chem. Mater.* 10: 1214-19; Enustun & Turkevich, (1963) *J. Am. Chem. Soc.* 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticle Size

In various aspects, methods provided include those utilizing nanoparticles which range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or amount surface area that can be derivatized as described herein.

Oligonucleotide Features

Oligonucleotides can be either functionalized on a nanoparticle, an oligonucleotide-binding molecule, or as a hairpin compound.

Each nanoparticle utilized in the methods provided has a plurality of oligonucleotides attached to it. As a result, each nanoparticle-oligonucleotide conjugate has the ability to hybridize to a second oligonucleotide functionalized on a second nanoparticle, and/or, when present, a free oligonucleotide, having a sequence sufficiently complementary. In one aspect, methods are provided wherein each nanoparticle is functionalized with identical oligonucleotides, i.e., each oligonucleotide attached to the nanoparticle has the same length and the same sequence. In other aspects, each nanoparticle is functionalized with two or more oligonucleotides which are not identical, i.e., at least one of the attached oligonucleotides differ from at least one other attached oligonucleotide in that it has a different length and/or a different sequence.

In one aspect, oligonucleotides are designed which are identical to, or sufficiently homologous to, oligonucleotide complexes that exist in nature, thereby allowing identification of compounds that interact selectively with a naturally-occurring complex. Accordingly, oligonucleotides are in general prepared with knowledge of the known sequences. Methods of making oligonucleotides of a predetermined sequence are well-known. See, for example, Sambrook et al., *Molecular Cloning: A Laboratory Manual* (2nd ed. 1989) and F. Eckstein (ed.) *Oligonucleotides and Analogues,* 1st Ed. (Oxford University Press, New York, 1991). Solid-phase synthesis methods are contemplated for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Alternatively, oligonucleotides are selected from a library. Preparation of libraries of this type is well know in the art. See, for example, US Patent Publication No. 20050214782.

The term "oligonucleotide" as used herein includes modified forms as discussed herein as well as those otherwise known in the art which are used to regulate gene expression. Likewise, the term "nucleotides" as used herein is interchangeable with modified forms as discussed herein and otherwise known in the art. In certain instances, the art uses the term "nucleobase" which embraces naturally-occurring nucleotides as well as modifications of nucleotides that can be polymerized. Herein, the terms "nucleotides" and "nucleobases" are used interchangeably to embrace the same scope unless otherwise noted.

In various aspects, methods include oligonucleotides which are DNA oligonucleotides, RNA oligonucleotides, or combinations of the two types. Modified forms of oligonucleotides are also contemplated which include those having at least one modified internucleotide linkage. In one embodiment, the oligonucleotide is all or in part a peptide nucleic acid. Other modified internucleoside linkages include at least one phosphorothioate linkage. Still other modified oligonucleotides include those comprising one or more universal bases. "Universal base" refers to molecules capable of substituting for binding to any one of A, C, G, T and U in nucleic acids by forming hydrogen bonds without significant structure destabilization. The oligonucleotide incorporated with the universal base analogues is able to function as a probe in hybridization, as a primer in PCR and DNA sequencing. Examples of universal bases include but are not limited to 5'-nitroindole-2'-deoxyribo side, 3-nitropyrrole, ino sine and pypoxanthine.

Modified Backbones: Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide."

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, , U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

Modified Sugar and Internucleoside Linkages: In still other embodiments, oligonucleotide mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

In still other embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligo consists of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO($BH_3$)—, —P(O,S)—, —P(S)$_2$—, —PO(R")—, —PO($OCH_3$)—, and —PO($NHR^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$, —O—$CH_2$—S—, —S—$CH_2$—O—, —$CH_2$—$CH_2$—S—, —O—$CH_2$—$CH_2$—S—, —S—$CH_2$—CH=(including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—; —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO($OCH_3$)—O—, —O—PO(O $CH_2CH_3$)—O—, —O—PO(O) $CH_2CH_2$S—R)—O—, —O—PO($BH_3$)—O—, —O—PO($NHR^N$)—O—, —O—P(O)$_2$—$NR^H$ H—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—O—P(—O,S)—O—, —O—P(S)$_2$—O—, —$NR^H$P(O)$_2$—O—, —O—P(O,$NR^H$)—O—, —O—PO(R")—O—, —O—PO($CH_3$)—O—, and —O—PO($NHR^N$)—O—, where RH is selected form hydrogen and $C_{1-4}$-alkyl, and R" is selected from $C_{1-6}$-alkyl and phenyl, are contemplated. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443.

Still other modified forms of oligonucleotides are described in detail in U.S. Patent Publication No. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. Other modifications include 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples herein below.

Still other modifications include 2'-methoxy (2'-O—$CH_3$), 2'-aminopropoxy (2'- $OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Bases: Oligonucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido [5,4-b][1,4]benzoxazin-2(3H)-one), phenothiazine cytidine (1H-pyrimido[5,4-b][1,4]benzothiazin-2 (3H)-one), G-clamps such as a substituted phenoxazine cytidine (e.g. 9-(2-aminoethoxy)-H-pyrimido[5,4-b][1,4] benzox-azin-2(3H)-one), carbazole cytidine (2H-pyrimido [4,5-b]indol-2-one), pyridoindole cytidine (H-pyrido[3',2':4, 5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687, 808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. No. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

Nanoparticles for use in the methods provided are functionalized with an oligonucleotide, or modified form thereof, which is from about 5 to about 100 nucleotides in length. Methods are also contemplated wherein the oligonucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides in length are contemplated.

"Hybridization," which is used interchangeably with the term "complex formation" herein, means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art.

In various aspects, the methods include use of two or three oligonucleotides which are 100% complementary to each other, i.e., a perfect match, while in other aspects, the individual oligonucleotides are at least (meaning greater than or equal to) about 95% complementary to each over the all or part of length of each oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to each other.

It is understood in the art that the sequence of the oligonucleotide used in the methods need not be 100% complementary to each other to be specifically hybridizable. Moreover, oligonucleotide may hybridize to each other over one or more segments such that intervening or adjacent segments are not involved in the hybridization event (e.g., a loop structure or hairpin structure). Percent complementarity between any given oligonucleotide can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Oligonucleotide Attachment

Oligonucleotides contemplated for use in the methods include those bound to the nanoparticle through any means. Regardless of the means by which the oligonucleotide is attached to the nanoparticle, attachment in various aspects is effected through a 5' linkage, a 3' linkage, some type of internal linkage, or any combination of these attachments.

In one aspect, the nanoparticles, the oligonucleotides or both are functionalized in order to attach the oligonucleotides to the nanoparticles. Methods to functionalize nanoparticles and oligonucleotides are known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry*, Houston, Tex., pages 109-121 (1995). See also, Mucic et al. *Chem. Commun.* 555-557 (1996) which describes a method of attaching 3' thiol DNA to flat gold surfaces. The alkanethiol method can also be used to attach oligonucleotides to other metal, semiconductor and magnetic colloids and to the other types of nanoparticles described herein. Other functional groups for attaching oligonucleotides to solid surfaces include phosphorothioate groups (see, for example, U.S. Pat. No. 5,472,881 for the binding of oligonucleotide-phosphorothioates to gold surfaces), substituted alkylsiloxanes (see, for example, Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., Anal. Chem., 67, 735-743 for binding of aminoalkylsiloxanes and for similar binding of mercaptoaklylsiloxanes). Oligonucleotides with a 5' thionucleoside or a 3' thionucleoside may also be used for attaching oligonucleotides to solid surfaces. The following references describe other methods which may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec et al., *J. Phys. Chem.*, 92, 2597 (1988) (rigid phosphates on metals).

U.S. Pat. Nos. 6,767,702 and 6,750,016 and International Patent Publication Nos. WO 2001/051665 and WO 2001/073123 describe oligonucleotides functionalized with a cyclic disulfide. The cyclic disulfides in certain aspects have 5 or 6 atoms in their rings, including the two sulfur atoms. Suitable cyclic disulfides are available commercially or are synthesized by known procedures. Functionalization with the reduced forms of the cyclic disulfides is also contemplated.

In certain aspects of cyclic disulfide functionalization, oligonucleotides are attached to a nanoparticle through one or more linkers. In one embodiment, the linker comprises a hydrocarbon moiety attached to a cyclic disulfide. Suitable hydrocarbons are available commercially, and are attached to the cyclic disulfides. The hydrocarbon moiety is, in one aspect, a steroid residue. Oligonucleotide-nanoparticle conjugates prepared using linkers comprising a steroid residue attached to a cyclic disulfide are more stable to thiols compared to conjugates prepared using alkanethiols or acyclic disulfides as the linker, and in certain instances, the oligonucleotide-nanoparticle conjugates have been found to be 300 times more stable. In certain embodiments, the two sulfur atoms of the cyclic disulfide are close enough together so that both of the sulfur atoms attach simultaneously to the nanoparticle. In other aspects, the two sulfur atoms are adjacent each other. In aspects where utilized, the hydrocarbon moiety is large enough to present a hydrophobic surface screening the surfaces of the nanoparticle.

In other aspects, a method for attaching oligonucleotides onto a surface is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide conjugates with enhanced stability and selectivity. The process comprises providing oligonucleotides, in one aspect, having covalently bound thereto a moiety comprising a functional group which can bind to the nanoparticles. The moieties and functional groups are those that allow for binding (i.e., by chemisorption or covalent bonding) of the oligonucleotides to nanoparticles. For example, oligonucleotides having an alkanethiol, an alkanedisulfide or a cyclic disulfide covalently bound to their 5' or 3' ends bind the oligonucleotides to a variety of nanoparticles, including gold nanoparticles.

EXAMPLES

Au NPs (13 nm) were synthesized according to literature procedures (Frens, *Nature Phys. Sci.*, 241, 20-22 (1973)). All oligonucleotides were purchased from Integrated DNA Technologies, Inc. (IDT, Coralville, Iowa). Dithiothreitol (DTT) was purchased from Pierce Biotechnology, Inc. (Rockford, Ill.). DNA binding molecules and all other reagents were purchased from Sigma-Aldrich (St. Louis, Mo.). Melting data was collected on a Cary 500 or Cary 5000 UV-Vis spectrophotometer. Au NPs were functionalized with thiolated DNA according to the protocol outlined in reference (Hurst, et al. *Anal. Chem.*, 78, 8313-8318 (2006)).

Au NPs were functionalized with complementary oligonucleotides DNA-1 (3' SH $A_{10}$ AAT AAC AAT 5'; SEQ ID NO: 1) and DNA-2 (3' SH $A_{10}$ ATT GTT ATT 5'; SEQ ID NO: 2) (AT-rich sequences) denoted as NP-1 and NP-2. DAPI was combined with six short sequences of hairpin DNA (5' CG XXXXX CAAAAAG X'X'X'X'X' CG 3'; SEQ ID NOs: 3-8) (Table 1). The sequence of the loop region of these hairpins is held constant, while the 5-base duplex stem region is variable (denoted X and X'), consisting of a different number of GC pairs (0 (all AT) -5 (all GC)). The HP DNA are designated throughout according to the number of GC pairs in its variable region (e.g., 0 GC, 1 GC, etc). When DAPI is added to a solution containing NP-1, NP-2, and the HP DNA, it can either bind to the duplex interconnects between the Au NPs or the duplex stem of the HP DNA depending on its relative affinity for each. The $T_m$ of the nanoparticle aggregates varies as a result of the change in the effective concentration of DAPI in solution. Importantly, the $T_m$ of the HP DNA in the presence of DAPI is much higher than that of the nanoparticle aggregates. Therefore, additional DAPI is not released from its bound state in the stem duplexes as the assay progresses.

Figure 5:
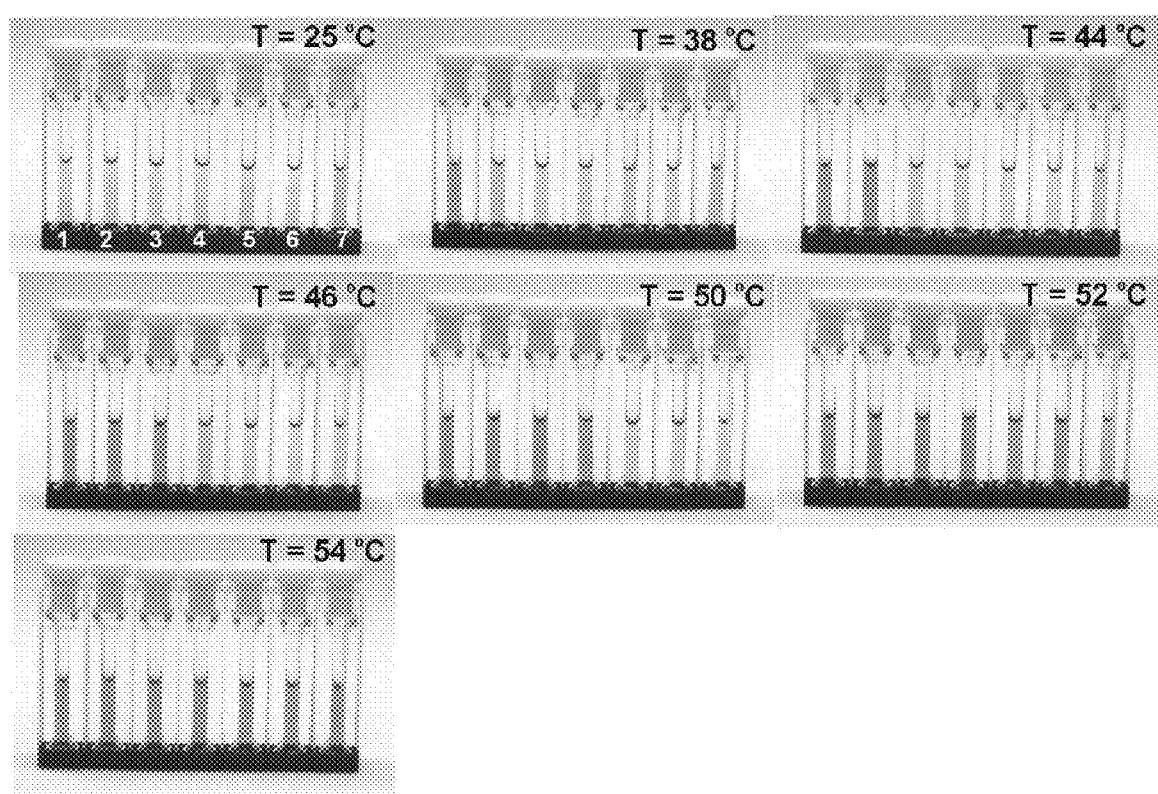
FIG. 5 shows images of cuvettes containing 0 GC, 1 GC, 2 GC, 3 GC, 4 GC, 5 GC samples (with DAPI) (1-6, respectively) and a control sample (no HP DNA) (7) over a range of temperatures.

An advantage of the disclosed method is that it offers the potential for naked eye detection. For DAPI (an A-T selective binding molecule), with the exception of the 4 GC (SEQ ID NO: 7) and 5 GC (SEQ ID NO: 8) samples, which have $T_m$s within 1° C. of each other (and therefore similar binding affinities for DAPI), the binding strength of DAPI to a particular sequence of HP DNA can be compared using a temperature gradient (FIG. 5). At room temperature, all of the Au NP samples in cuvettes 1-7 are aggregated and exhibit a blue-purple color. As the temperature is raised and the $T_m$ of the aggregates is reached, the aggregates disperse and the samples become bright red in color. At 38° C., a red color is observed only in cuvette 1 (the 0 GC sample; SEQ ID NO: 3), which contains the HP DNA for which DAPI has the highest binding affinity. At slightly higher temperatures, the samples in cuvettes 2-4 (1 GC-3 GC samples, respectively; SEQ ID NOs: 4 to 6) undergo a color change in turn as the binding affinity of DAPI for the HP DNA of interest decreases. The color change for the samples in cuvettes 5 and 6 (4 GC and 5 GC samples, respectively; SEQ ID NOs: 7 and 8) happens almost simultaneously around 52° C. The Au NP aggregates in cuvette 7 (no HP DNA) are the most stable and melt at approximately 53° C. Using this simple, naked-eye detection method, the trend in DAPI binding selectivity for the HP DNA was correctly determined to be 0 GC>1 GC>2 GC>3 GC>4 GC and 5 GC, which is consistent with the control experiments involving instrumental analysis of each HP with DAPI.

To initiate the assay of DAPI sequence selectivity, NP-1 (13 nm Au NP modified on its surface with SEQ ID NO: 1) and NP-2 (13 nm Au NP modified on its surface with SEQ ID NO: 2) each were adjusted to a concentration of 1.5 nM (3 nM total Au NP concentration, using $\epsilon$=2.40×108 L/(mol*cm)), in 0.1 M NaCl, 10 mM phosphate buffer (PB) (pH=7). The concentration of DAPI and HP DNA each were brought to 5 µM (1:1 DAPI:HP DNA). After their preparation, the samples were allowed to incubate overnight (about 12 hr) at room

TABLE 1

Figure 3:
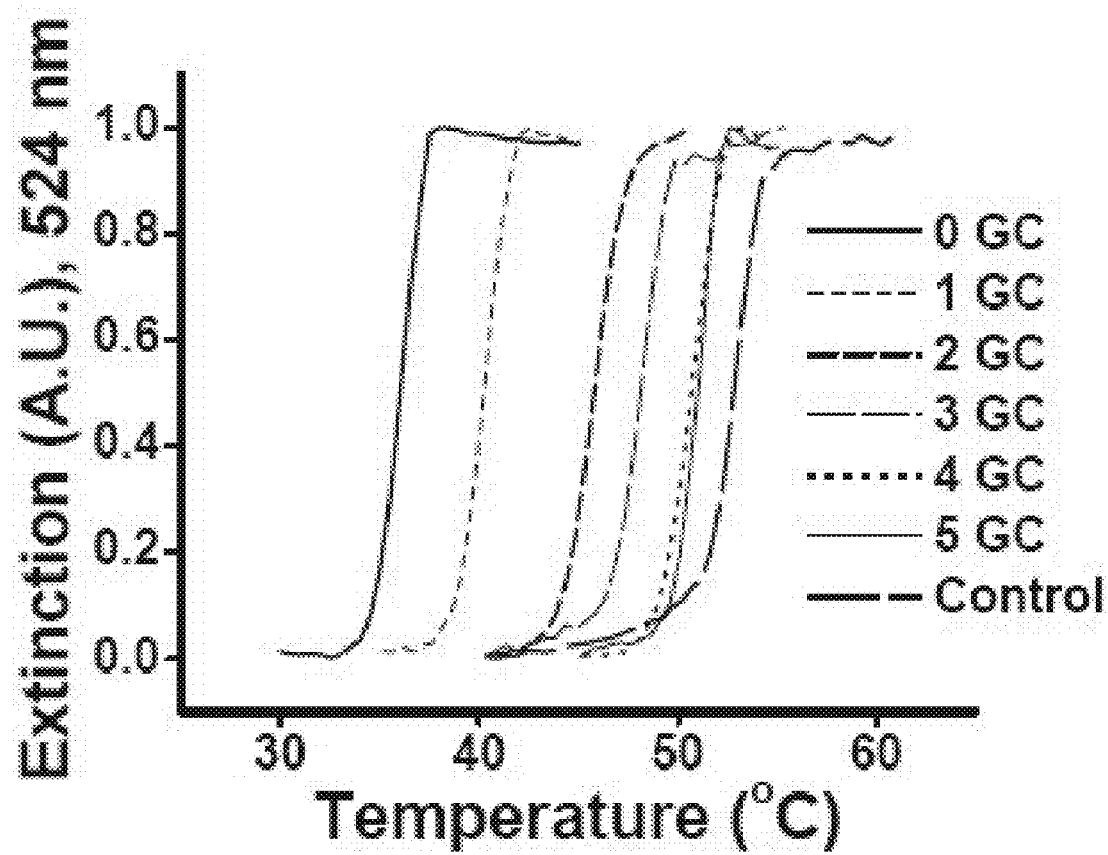
FIG. 3 shows normalized melting curves for aggregates of NP-1 and NP-2 with 5 μM DAPI and 5 μM HP DNA (0 GC-5 GC, 1:1 HP:DAPI). The curve denoted Control contains no HP DNA.

|  | Stem Sequence (XXXXX X'X'X'X'X') | NP $T_m$ (° C.) | HP $T_m$ (5 µM) (° C.) | HP $T_m$ (with DAPI, 1:1) (° C.) | Δ HP $T_m$ (° C.) |
|---|---|---|---|---|---|
| 0 GC | ATAAT TATTA SEQ ID NO: 3 | 36.1 | 51.0 | 79.1 | 28.1 |
| 1 GC | ATATG TATAC SEQ ID NO: 4 | 40.3 | 55.5 | 75.9 | 20.4 |
| 2 GC | CATTG GTAAC SEQ ID NO: 5 | 45.8 | 64.8 | 76.0 | 11.2 |
| 3 GC | ATCCG TAGGC SEQ ID NO: 6 | 48.2 | 70.7 | 79.4 | 8.7 |
| 4 GC | GCGCT CGCGA SEQ ID NO: 7 | 50.7 | 78.4 | 81.9 | 3.5 |
| 5 GC | CGCGC GCGCG SEQ ID NO: 8 | 51.1 | 85.8 | 88.8 | 3.0 |
| Control | NA | 52.9 | NA | NA | NA | temperature in order to reach equilibrium. During this time, NP-1 and NP-2 hybridized and formed a polymeric aggregate that settled to the bottom of the cuvette, leaving a colorless supernatant. Next, the samples were heated at a rate of 1.0° C./min with stirring, while being monitored at the extinction maximum of the dispersed Au NPs (λ=524 nm). In this manner, a melting curve for the duplex DNA holding the aggregate together was obtained (FIG. 3). In the control sample, a DAPI concentration having a maximum observable shift in $T_m$ ($T_m$=52.9° C.) was used. Above this concentration, the $T_m$ remained constant, presumably because the DNA links are fully loaded with DAPI. The $T_m$ of the nanoparticle aggregates decreased when HP DNA was added. The magnitude of the decrease, however, depended on the number of GC pairs in the HP duplex stem region. The greatest decrease in $T_m$ was observed when SEQ ID NO: 3 (0 GC) was used ($T_m$=36.1° C.), while when SEQ ID NO: 8 (5 GC) was used the melting temperature of the Au NP duplex of NP-1 and NP-2 maintained a $T_m$ of 51.1° C. (see FIG. 3 and Table 1). This result corresponds to DAPI's known greater affinity for hairpins with more AT pairs, and, correspondingly, less GC pairs (Ren, et al. *Biochemistry*, 38, 16067-16075 (1999)). As a result, as more AT pairs are introduced in the HP stem region, DAPI preferentially binds the HP DNA and, since less DAPI is available to react with the Au NPs, the nanoparticle $T_m$ decreases. $T_m$s separated by typically about 1-3° C. were observed for HP DNA possessing the same number of GC base pairs but arranged in a different order (Table 2).

TABLE 2

| Stem Sequence | NP $T_m$ (° C.) | Stem Sequence | NP $T_m$ (° C.) |
|---|---|---|---|
| 0 GC ATAAT TATTA SEQ ID NO: 3 | 36.1 | 3 GC ATCCG TAGGC SEQ ID NO: 6 | 48.2 |
| AATTA TTAAT SEQ ID NO: 9 | 35.0 | AGCTG TCGAC SEQ ID NO: 12 | 51.5 |
| 1 GC AGATT TCTAA SEQ ID NO: 4 | 40.3 | 4 GC GCGCT CGCGA SEQ ID NO: 7 | 50.7 |
| ATATG TATAC SEQ ID NO: 10 | 39.4 | AGCCG TCGGC SEQ ID NO: 13 | 51.3 |
| 2 GC CATTG GTAAC SEQ ID NO: 5 | 45.8 | 5 GC CGCGC GCGCG SEQ ID NO: 8 | 51.1 |
| ATCTG TAGAC SEQ ID NO: 11 | 42.6 | GGCGG CCGCC SEQ ID NO: 14 | 50.9 |

Figure 6:
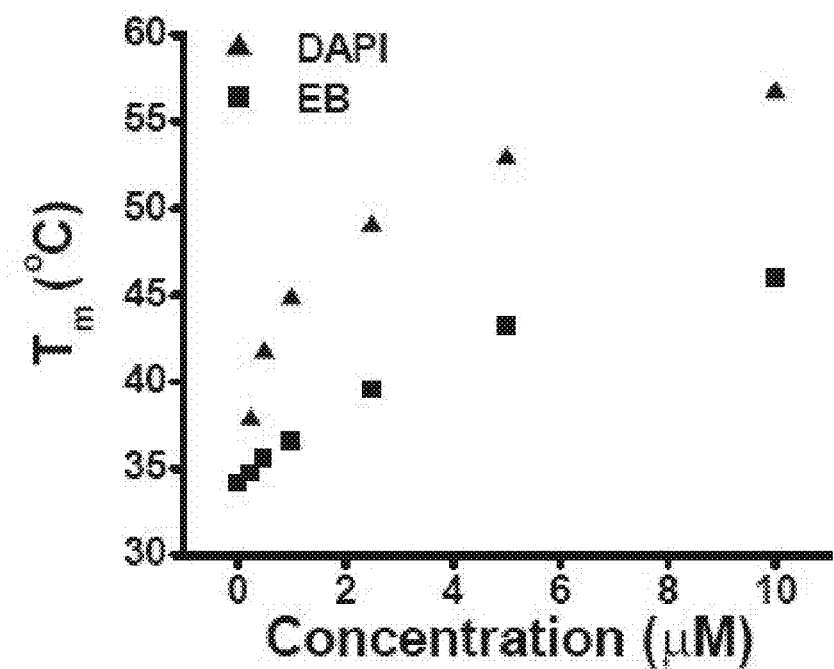
FIG. 6 shows a plot melting temperature ($T_m$) vs. DAPI concentration and EB concentration.
Figure 7:
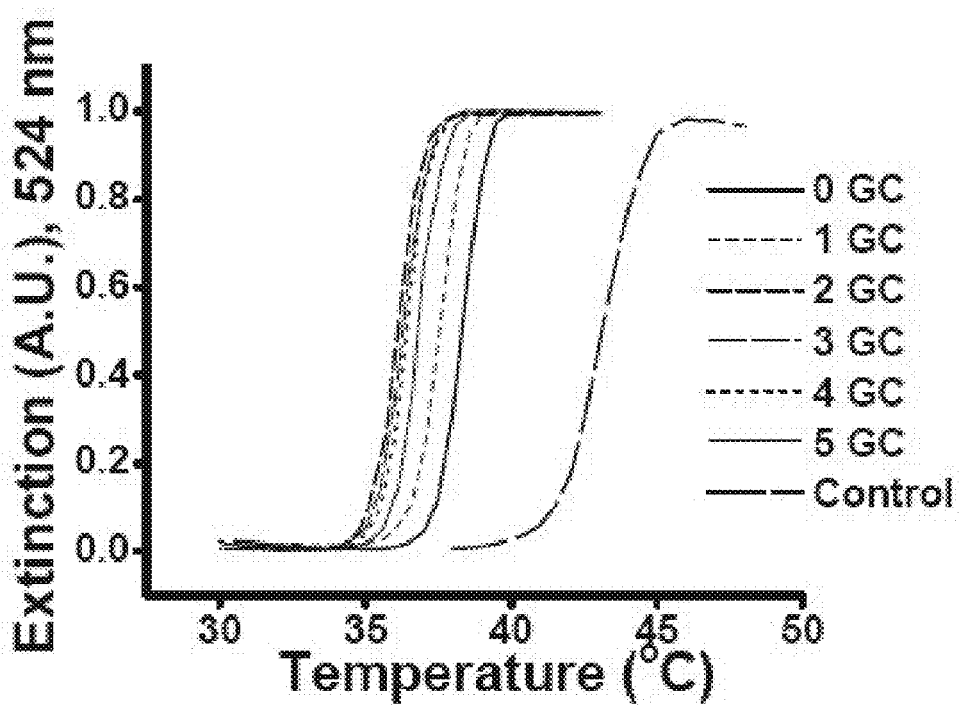
FIG. 7 shows normalized melting curves for aggregates of NP-1 and NP-2 with 5 μM EB and 5 μM HP DNA (0 GC-5 GC, 1:1 HP:EB). The curve denoted Control contains no HP DNA.

The $T_m$ of the Au NP aggregates also can be affected by the concentration of ethidium bromide (EB) (a non-specific DNA binder) in solution (Bailly, et al. *J. Molecul. Recogn.*, 5, 155-171 (1992)). However, for any given concentration, the increase in $T_m$ for a sample containing EB is less than that for a sample containing DAPI (see FIG. 6). When EB was studied with the 6 HP DNA (SEQ ID NOs: 3-8) using the same protocol as for DAPI, the Au NP $T_m$s of all the samples differed by less than 2° C. and followed no particular trend regarding sequence (Table 3 and FIG. 7). The $T_m$ of these samples, however, was lower than that of the control sample containing only NP-1, NP-2 and EB (5 μM). This result confirms that EB has a relatively non-specific affinity for any of the DNA sequences studied here.

TABLE 3

| | Stem Sequence (XXXXX X'X'X'X'X') | NP $T_m$ (° C.) | HP $T_m$ (5 μM) (° C.) | HP $T_m$ (with EB, 1:1) (° C.) | Δ HP $T_m$ (° C.) |
|---|---|---|---|---|---|
| 0 GC | ATAAT TATTA SEQ ID NO: 3 | 33.6 | 51.0 | 62.0 | 11.0 |
| 1 GC | ATATG TATAC SEQ ID NO: 4 | 38.3 | 55.5 | 66.6 | 11.1 |
| 2 GC | CATTG GTAAC SEQ ID NO: 5 | 37.6 | 64.8 | 74.5 | 9.7 |
| 3 GC | ATCCG TAGGC SEQ ID NO: 6 | 36.1 | 70.7 | 80.7 | 10.0 |
| 4 GC | GCGCT CGCGA SEQ ID NO: 7 | 36.3 | 78.4 | 87.3 | 8.9 |
| 5 GC | CGCGC GCGCG SEQ ID NO: 8 | 36.4 | 85.8 | 89.7 | 3.9 |
| Control | | NA | 43.1 | NA | NA |

Figure 8:
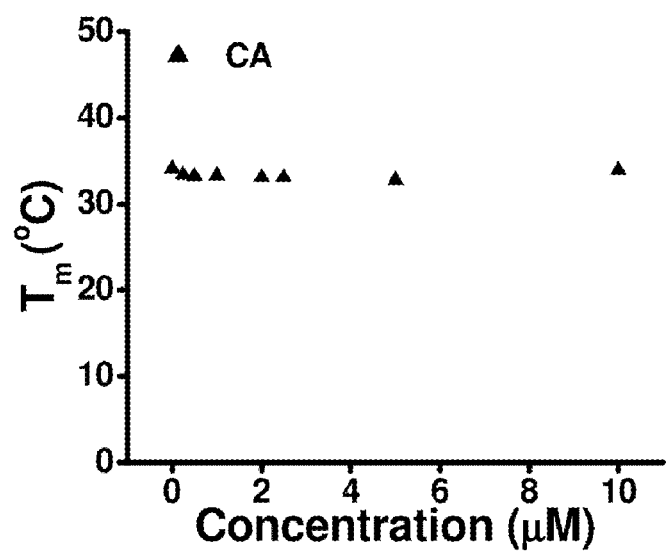
FIG. 8 shows a plot of melting temperature ($T_m$) (monitored at $\lambda$=524 nm) vs. Chromomycin A concentration (between 0 and 10 μm) for aggregates of NP-1 and NP-2 (AT-rich).
Figure 9:
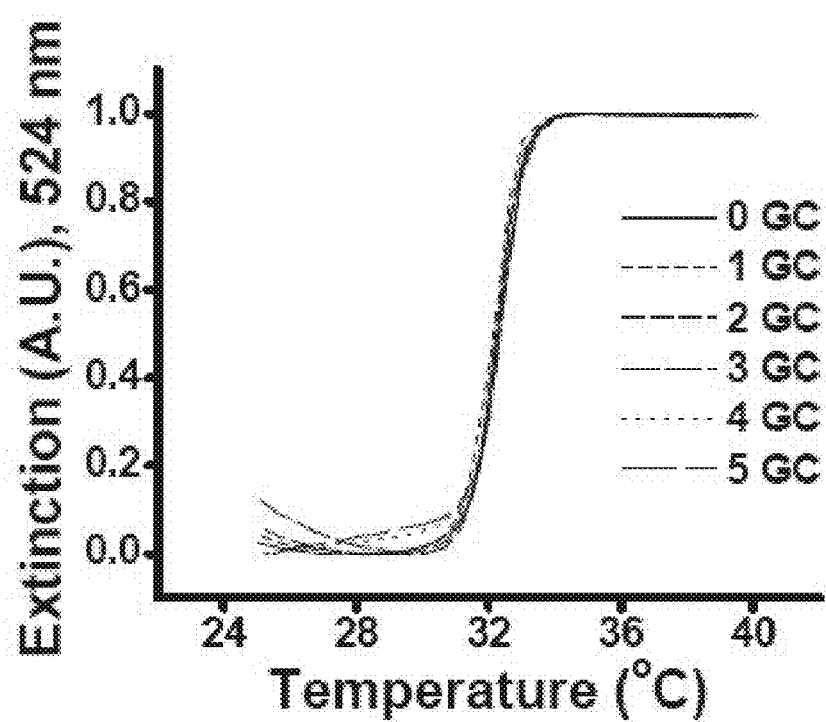
FIG. 9 shows normalized melting curves for aggregates of NP-1 and NP-2 (AT-rich) with 5 μM Chromomycin A and 5 μM HP DNA (0 GC-5 GC, 1:1 HP:Chromomycin A)

In contrast to DAPI and EB, the $T_m$ of the Au NP aggregates is not affected by the concentration of chromomycin A (CA) (a GC-specific binder) in solution (FIG. 8) (Ren, et al. *Biochemistry* 38, 16067-16075 (1999)). As a result, when CA was investigated with the 6 HP DNA using the same protocol, the Au NP $T_m$s of all the samples were approximately equal to the sample containing only aggregates of NP-1 and NP-2 (FIG. 9). This result suggests that CA is GC-specific. In order to further investigate the sequence specificity of a GC binding molecules, such as CA, the DNA sequences on the Au NPs can be changed from ones that are AT-rich to ones that are GC-rich. Then, the assay would proceed for these types of intercalators in an analogous fashion.

Control experiments were performed where the $T_m$ of the free HP DNA was evaluated (at λ=260 nm) both with and without the DNA-binding molecules of interest (no Au NPs) (for DAPI (Table 1) and EB (Table 3)). A larger difference between the $T_m$ of the free HP DNA and the $T_m$ of the same HP in the presence of the intercalator suggests a greater affinity of the intercalator for a given HP sequence. The results of these control experiments correlated with the trends determined from the nanoparticle assay, and were consistent with literature trends based upon, for example, competition dialysis and electric linear dichroism (see, e.g., Ren, et al. *Biochemistry*, 38, 16067-16075 (1999)and Bailly, et al. *J. Molecul. Recogn.*, 5, 155-171(1992)).

From the foregoing it will be appreciated that, although specific embodiments of the invention have been described herein for purposes of illustration, various modifications may be made without deviating from the spirit and scope of the invention.

What is claimed:

1. A method of assessing selectivity of a destabilizing oligonucleotide-binding molecule comprising:

a) heating a first mixture comprising (1) a first complex comprising a first functionalized nanoparticle and a second functionalized nanoparticle, (2) a first hairpin oligonucleotide, and (3) the destabilizing oligonucleotide-binding molecule to determine a first melting temperature of the first complex in the first mixture, b) comparing the first melting temperature of the first complex in the first mixture to a second melting temperature of the first complex in a second mixture comprising (1) the first complex, (2) a second different hairpin oligonucleotide; and (3) the destabilizing oligonucleotide-binding molecule, wherein (i) a higher first melting temperature than the second melting temperature indicates stronger selectivity of the destabilizing oligonucleotide-binding molecule compound for the first hairpin oligonucleotide than for the second hairpin oligonucleotide, (ii) a lower first melting temperature than second melting temperature indicates a stronger selectivity of the destabilizing oligonucleotide-binding molecule for the second hairpin oligonucleotide than for the first hairpin oligonucleotide, and (iii) a first melting temperature essentially equal to the second melting temperature indicates essentially equal selectivity of the destabilizing oligonucleotide-binding molecule for the second hairpin oligonucleotide and the first hairpin oligonucleotide; and the first functionalized nanoparticle comprises a first oligonucleotide on at least a portion of the first nanoparticle surface and the second functionalized nanoparticle comprises a second oligonucleotide on at least a portion of the second nanoparticle surface, and the first oligonucleotide is sufficiently complementary to the second oligonucleotide to hybridize.

2. A method of assessing selectivity of a stabilizing oligonucleotide-binding molecule comprising:

a) heating a first mixture comprising (1) a first complex comprising a first functionalized nanoparticle and a second functionalized nanoparticle, (2) a first hairpin oligonucleotide, and (3) the stabilizing oligonucleotide-binding molecule to determine a first melting temperature of the first complex in the first mixture, b) comparing the first melting temperature of the first complex in the first mixture to a second melting temperature of the first complex in a second mixture comprising (1) the first complex, (2) a second different hairpin oligonucleotide; and (3) the stabilizing oligonucleotide -binding molecule, wherein (i) a higher first melting temperature than the second melting temperature indicates stronger selectivity of the stabilizing oligonucleotide-binding molecule compound for the second hairpin oligonucleotide than for the first hairpin oligonucleotide, (ii) a lower first melting temperature than second melting temperature indicates a stronger selectivity of the stabilizing oligonucleotide-binding molecule for the first hairpin oligonucleotide than for the second hairpin oligonucleotide, and (iii) a first melting temperature essentially equal to the second melting temperature indicates essentially equal selectivity of the stabilizing oligonucleotide-binding molecule for the second hairpin oligonucleotide and the first hairpin oligonucleotide; and the first functionalized nanoparticle comprises a first oligonucleotide on at least a portion of the first nanoparticle surface and the second functionalized nanoparticle comprises a second oligonucleotide on at least a portion of the second nanoparticle surface, and the first oligonucleotide is sufficiently complementary to the second oligonucleotide to hybridize.

3. The method of claim 1, wherein the first oligonucleotide or second oligonucleotide is DNA.

4. The method of claim 1, wherein the first oligonucleotide and second oligonucleotide are DNA.

5. The method of claim 1, wherein the first oligonucleotide or the second oligonucleotide is a modified oligonucleotide.

6. The method of claim 1, wherein the first oligonucleotide and the second oligonucleotide are modified oligonucleotides.

7. The method of claim 1, wherein the first hairpin oligonucleotide or the second hairpin oligonucleotide is DNA.

8. The method of claim 1, wherein the first hairpin oligonucleotide and the second hairpin oligonucleotide are DNA.

9. The method of claim 1, wherein the first hairpin oligonucleotide or the second hairpin oligonucleotide is a modified oligonucleotide.

10. The method of claim 1, wherein the first hairpin oligonucleotide and the second hairpin oligonucleotide are modified oligonucleotides.

11. The method of claim 1, wherein the first nanoparticle and the second nanoparticle are gold nanoparticle.

12. The method of claim 11, wherein the first melting temperature is determined by detecting a blue-to-red color change associated with de-aggregation of the first gold nanoparticle and the second gold nanoparticle.

13. The method of claim 12, wherein the color change is detected without instrumentation.

14. The method of claim 11, wherein the first nanoparticle, second nanoparticle, or both have a diameter of about 13 nm to about 250 nm.

15. The method of claim 1, which is performed in a high throughput format.

* * * * *

UNITED STATES PATENT AND TRADEMARK OFFICE
CERTIFICATE OF CORRECTION

PATENT NO. : 7,807,372 B2  
APPLICATION NO. : 12/133243  
DATED : October 5, 2010  
INVENTOR(S) : Chad A. Mirkin et al.

Page 1 of 1

It is certified that error appears in the above-identified patent and that said Letters Patent is hereby corrected as shown below:

At column 1, line numbers 15-21, after "Statement of Governmental Support" please replace the paragraph with the following:

This invention was made with government support under Grant No. EEC-0647560 awarded by the National Science Foundation and Grant No. F49620-01-1-0401 awarded by the Air Force Office of Scientific Research and Grant No. 1U54 CA119341-01 awarded by the National Institutes of Health. The government has certain rights in the invention.

Signed and Sealed this
Eighth Day of March, 2011

David J. Kappos
*Director of the United States Patent and Trademark Office*

SEQUENCE LISTING

<160> NUMBER OF SEQ ID NOS: 14

<210> SEQ ID NO 1
<211> LENGTH: 19
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (19)..(19)
<223> OTHER INFORMATION: HS group is bound to the nucleotide in position 19

<400> SEQUENCE: 1
taacaataaa aaaaaaaaa                                              19

<210> SEQ ID NO 2
<211> LENGTH: 19
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (19)..(19)
<223> OTHER INFORMATION: HS group is bound to the nucleotide in position 19

<400> SEQUENCE: 2
ttattgttaa aaaaaaaaa                                              19

<210> SEQ ID NO 3
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 3
cgataatcaa aaagtatta                                              19

<210> SEQ ID NO 4
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 4
cgatatgcaa aaagtatac                                            19

<210> SEQ ID NO 5
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 5
cgcattgcaa aaaggtaac                                            19

<210> SEQ ID NO 6
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 6
cgatccgcaa aaagtaggc                                            19

<210> SEQ ID NO 7
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 7
cggcgctcaa aaagcgcga                                            19

<210> SEQ ID NO 8
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 8
cgcgcgccaa aaaggcgcg                                            19

<210> SEQ ID NO 9
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 9
cgaattacaa aaagttaat                                            19

<210> SEQ ID NO 10
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 10
cgatatgcaa aaagtatac                                            19

<210> SEQ ID NO 11
<211> LENGTH: 19

-continued

```
<212> TYPE: DNA
<213> ORGANISM: Artificial sequence
<220> FEATURE:
<223> OTHER INFORMATION: Synthetic polynucleotide

<400> SEQUENCE: 11
cgatctgcaa aaagtagac                                               19

<210> SEQ ID NO 12
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 12
cgagctgcaa aaagtcgac                                               19

<210> SEQ ID NO 13
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 13
cgagccgcaa aaagtcggc                                               19

<210> SEQ ID NO 14
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 14
cgggcggcaa aaagccgcc                                               19
```